United States Patent [19]
Allen et al.

[11] Patent Number: 5,979,658
[45] Date of Patent: Nov. 9, 1999

[54] PIN CARE KIT AND METHOD

[75] Inventors: Robert E. Allen, Lakewood; Jody S. Panian, Golden, both of Colo.

[73] Assignee: Brown Medical Indusrties, Spirit Lake, Iowa

[21] Appl. No.: 09/082,921

[22] Filed: May 21, 1998

[51] Int. Cl.[6] ............................................... A61F 13/00
[52] U.S. Cl. ........................... 206/572; 206/223; 206/229; 206/232; 206/438; 206/440; 206/568; 206/570; 604/290; 604/293; 604/304; 604/327; 606/53; 606/54; 606/59
[58] Field of Search ................................. 206/216, 223, 206/229, 232, 438, 440, 568, 570, 572, 828; 604/289, 290, 293, 304, 306, 310, 327; 606/53, 54, 59

[56] References Cited

U.S. PATENT DOCUMENTS

| | | | |
|---|---|---|---|
| 4,856,504 | 8/1989 | Yamamoto et al. | 606/59 |
| 5,080,661 | 1/1992 | Lavender et al. | 606/54 |
| 5,207,652 | 5/1993 | Kay | 604/180 |
| 5,281,221 | 1/1994 | Tadych | 606/53 |
| 5,447,492 | 9/1995 | Cartmell et al. | 602/58 |

*Primary Examiner*—Robert H. Harrison
*Attorney, Agent, or Firm*—Zarley, McKee, Thomte, Voorhees & Sease

[57] ABSTRACT

A kit for external fixation pin site care in conjunction with practicing a uniform and consistent standardized protocol to significantly reduce post-operative infection risk is provided. The kit contains labeled treatment materials to be used in the newly-designed, standard post-operative cleansing and infection treatment procedure. The result is significantly reduced incidences of infection at the pin/skin interface of patients.

9 Claims, 2 Drawing Sheets

PIN CARE KIT AND METHOD

BACKGROUND OF THE INVENTION

One of the most common complications encountered with external fixation devices is pin tract infection in post-operative patients. Treatments for this type of infection normally include oral antibiotics, hospitalization for administration of intravenous antibiotics, and in some cases, when the infection is severe treatment includes pin removal.

External fixator pin care currently employed ranges from doing nothing, to using ointments, to pouring saline on the pin sites several times daily, and to use of antiseptic lotions to cover pin sites, etc. The patients are usually warned that if there is any redness or pain around a pin site associated with the increase of purulent discharge, the patient is instructed to return to hospital or doctor for starting of a regimen of antibiotic treatment. Nevertheless, despite their continuing infection risk external fixator pins are known to provide definite and significant orthopedic aid; they are therefore used routinely.

The use of such external devices transfixed through bone to hold the position of a fracture indeed is not new. The pins in plaster method has been used for many years to hold bone fragments in proper position during the healing process. More recently, there has been increased utilization of multiple pins placed through one cortex or both cortices of bone, held by a unilateral, bilateral or circumferential fixation device. For example, Ilizarov circumferential fixation is used for lengthening or bone transport, and EBI® unilateral fixation is often used for forearm fractures. These fixators allow easy access to wounds, adjustments during the course of healing, and enhance functional use of the limb involved during healing.

With such devices as those above listed, the most common complication encountered is infection at the pin site. Commonly, hospitalization for intravenous antibiotics will occur over a five-day period and is quite expensive. The occurring high incidence of infection and common requirement for hospitalized treatment is a result of the lack of a uniform pin site care protocol which can be consistently and regularly practiced with a high degree of patient compliance. Indeed, a quick review of the literature indicates significant variations are noted in existing protocol designs, and that the majority demand large amounts of supplies, great expense, and much time on the part of the patient.

Some of the more common cleansing methods practiced to one degree or another in the known prior art are:

(1) Cleaning pin sites with tap or soap water, one to four times daily;

(2) Spraying each pin site with normal saline, using sterile syringes;

(3) Cleansing with 100% peroxide alone or in conjunction with a Betadine ointment;

(4) Pouring sodium chloride over the pin site four times daily;

(5) Applying antibacterial ointment or antiseptic ointment only;

(6) Changing dressings one or two times daily without specific cleaning of the pin site;

(7) Cleaning pin sites one to four times daily with Hibiclens or Betadine solution and covering with sponges or dressings; and (8) Showering.

The problems associated with these methods include cross-contamination of the pin sites, the sealing in of infectious process by ointments, allergies to the cleaning agents, skin irritations caused by the cleaning agents, availability of supplies, no specific contact person for problem solving, and the requirement for numerous clinic visits.

It can be seen that there is a continuing need for an uncomplicated and effective pin site care protocol which decreases infection risk and increases patient compliance. It is a primary object of this invention to fulfill this need.

Another object of this invention is to provide a low-cost kit and regimen that can use widely-available cleaning supplies.

Another object of the invention is to provide a clear and concise set of written instructions for patient education.

Yet another object of the present invention is to provide decreased need for post-operative medical intervention.

An even further object of the present invention is to provide universal treatment procedures from a single kit for circumferential fixators, unilateral fixators, pelvic fixators, halo-fixation, skeletal traction and Gardner-Wells fixation.

A further object of the present invention is to provide a kit which will allow for patient involvement in their own care in a manner that is more effective than the random treatment processes now commonly used for pin site care.

A still further objective is to provide all of the above objects using materials that are hypoallergenic and using solutions that do not cause allergic reactions in most patients.

SUMMARY OF THE INVENTION

Figure 1:
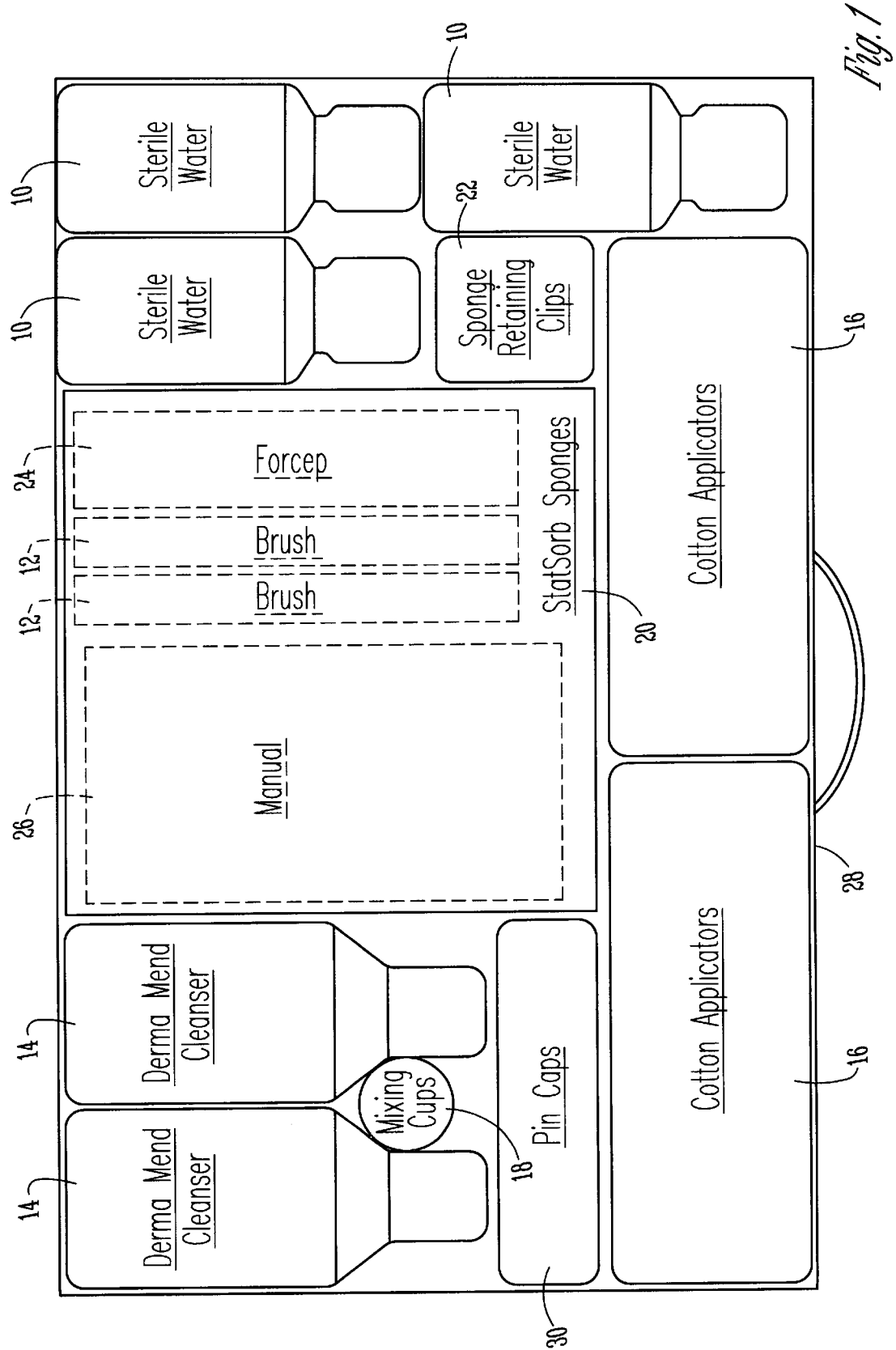
FIG. 1 is a plan view of a convenience kit compartmentalized to hold treatment materials, all conveniently packaged in the pin care kit.
Figure 2:
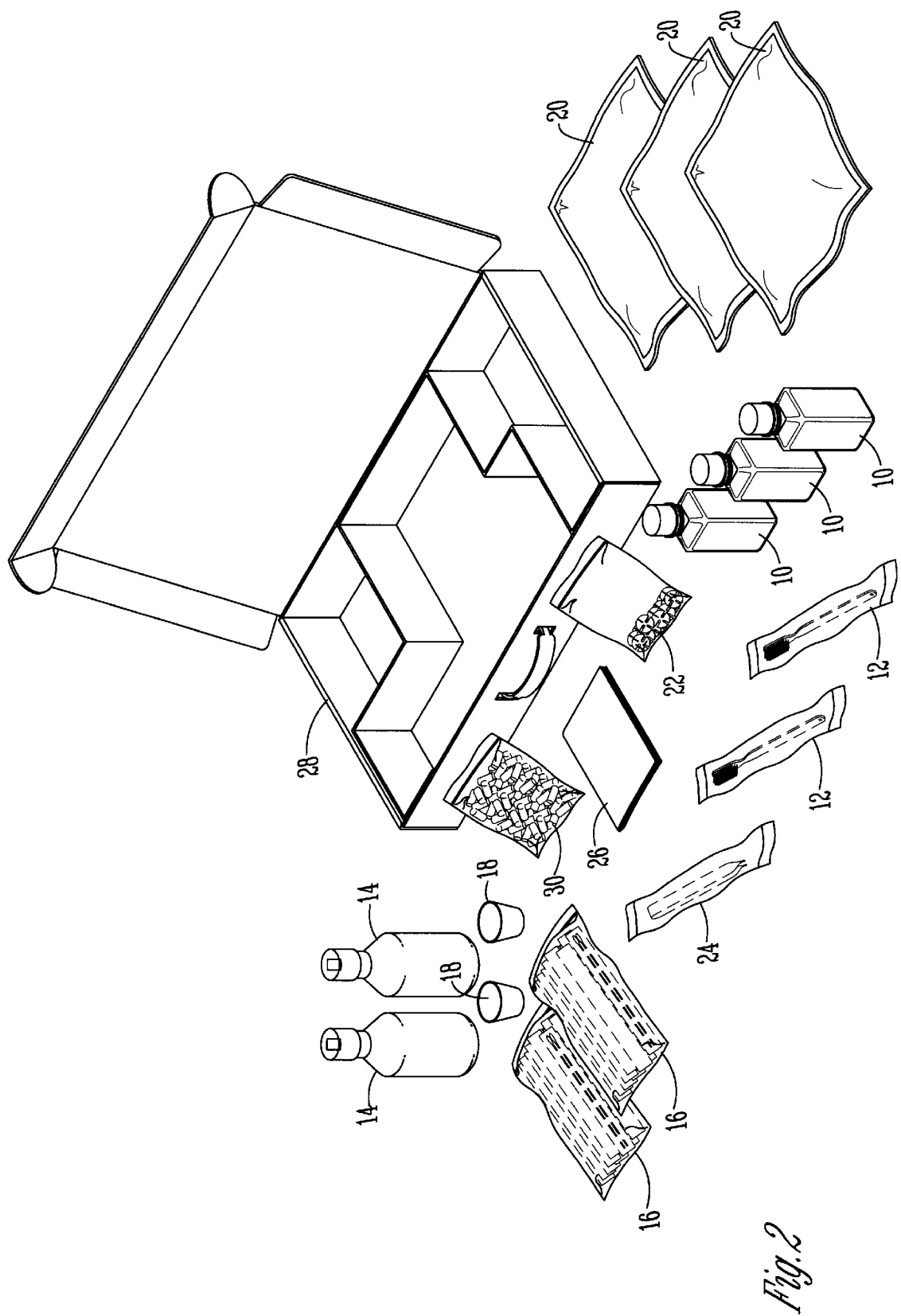
FIG. 2 is an exploded view of the kit and the refillable materials used in the kit, laid out to show the spatial arrangement.

This invention relates to a kit for pin care infection control, especially at the interface between pins of an external orthopedic fixator and a patient's skin. The kit decreases significantly the normal percentage of infection occurrences in post-operative patients. The kit is a sealable, refillable container with a series of compartments holding a plurality of labeled treatment materials for post-operative cleansing in accordance with a newly-designed procedure described in written instructions contained in the kit, which are correlated with the labeled materials in the kit.

DETAILED DESCRIPTION OF THE INVENTION

After a substantial period of trial and error, modifications of currently-used standardized protocols, and patient observations in treatments post-operatively, a standardized protocol was developed that utilizes the following practice steps.

1. A complete in-hospital, pre-operative and post-operative instruction session;

2. An instructional video for at-home review;

3. Pin site cleaning twice daily;

4. A daily log for entering times of each cleaning and tracking of any potential problems;

5. A refillable kit or bag generally containing:
   a. Sterile water 10;
   b. Small toothbrush 12;

c. Anti-microbial cleanser 14;

d. Sterile Q-tips 16;

e. Medicine cups 18;

f. Sponges 20 and clips 22 for each pin to be changed with each cleaning;

g. Forceps 24 for removing/inserting sponges 20;

6. Written instructions 26 including a specific list of complications of which the patient should be aware;

7. Specific follow-up instructions 26; and

8. A prescription recommendation for oral antibiotics and instructions on when to seek such medicinal treatment.

The preferred components of the pin care kit are the following:

1 Carrying and storage box 28;

1 Patient education video (not depicted);

1 Patient instruction manual, including daily log sheets 26;

1 Forceps 24;

2 Soft bristled brushes 12;

2 30 ml (1 ounce) medicine cups 18;

36 Pin caps 30;

36 Retainer clips 22;

150 Cotton-tipped applicators 16;

150 StatSorb™ sponges 20;

3 250 ml bottles sterile water 10; and 2 12-ounce bottles of anti-microbial cleanser 14.

The procedure using the above-labeled materials will generally involve cleaning the pin sites twice daily according to the following regimen with written instructions 26 that are contained in the kit 28.

Step 1—Remove retainer clips 22 and dispose of StatSorb™ sponges 20. Pour 15 ml (½ ounce) sterile water 10 into mixing cup 18. Dip soft-bristled brush 12 into sterile water 10 and lightly cleanse each pin site 360 degrees at the skin entry site. (Do not scrub). This will remove any drainage, dried blood or tissue build-up. (This is not the sterile cleansing step). Dip brush 12 in the cup 18 of sterile water 10 after each pin site is cleansed. Pour out remaining water and rinse both the brush 12 and cup 18 with tap water after all pin sites have been cleansed. (Never save the water in the cup). Allow each site to air dry.

Step 2—Pour 15 ml (½ ounce) anti-microbial cleanser 14 into the second mixing cup. Dip a sterile cotton-tipped applicator 16 into the cup 18 and lightly cleanse each pin site 360 degrees at the skin entry site. Use one sterile cotton-tipped applicator 16 per pin site and then dispose of applicator (this prevents "cross contamination"). Pour out the remaining anti-microbial cleanser 14 and rinse with tap water after all pin sites have been cleansed. Allow each site to air dry.

Step 3—After each pin site is cleansed, apply a new StatSorb™ sponge 20 with the forceps 24 and reapply the retainer clip 22. (The clip 22 will hold the sponge 20 in place and help minimize "micromotion" at the pin site and decrease skin irritation). When the pin site stops draining, continue to use StatSorb™ sponges 20 to help minimize "micromotion" at the pin site. ("Micromotion" at the pin site can irritate the pin site and possibly help cause an infection).

Step 4—Record any concerns on the Daily Log Sheet 26 such as redness, excessive drainage, increased pin site pain, etc. This will help you communicate your progress as well as any potential developing problem to your physician.

What to do:

1. Cleanse pin sites twice daily;
2. Record all cleansing times and concerns on Daily Log Sheet 26;
3. Call for supplies or to express concerns. What to watch for: (1) excessive drainage; (2) increased pin site pain; (3) calf or chest pain; (4) excessive bleeding; (5) ongoing anxiety; (6) chills or fever; (7) breathing problems; (8) increased swelling; (9) increased heat; (10) pin site redness; (11) pin site red streaks; and (12) pin site skin tension.

The patient should be given a prescription for oral antibiotics in case a pin site infection develops. Should any of the above symptoms occur, the patient is instructed to call his physician's office.

The unique procedure of this pin care kit 28 and care system is that it allows a simple, yet comprehensive protocol and set of standard supplies to be used by the external fixation device patient to manage his or her own pin site wounds at home. If used, it has been successfully demonstrated as significantly decreasing infection risk with any external fixation device, including Ilizarov™, Orthofix™, DynaFix™, Hoffmann II™, Monotube Fixator™, Monticelli Spinelli™ and OrthoFrame™.

Prior to use of the kit 28 it is preferred that the patient be provided a video which is initially viewed, demonstrating the proper protocol. Any potential difficulties are identified and solutions discussed in the video. Depending upon the hospital stay, the first and second day of cleansings are done with the patient and the family. The log 26 is again reviewed, the post-discharge course is discussed, the patient is familiarized with complications to look for, and the specific contact person designated for problems, prescriptions and refill supplies for the kit 28. The patient makes his or her regular visit to the physician as indicated, and indeed the instructions are such that most of the discussions can occur with a physician's assistant, freeing up physician time.

The following examples are offered to illustrate the effectiveness of the kit 28 of the present invention in decreasing infection risk in comparison with published literature reports for convention pin care techniques.

EXAMPLES

Bassett & Morris describe patient infection using the Ilizarov technique in an article entitled "The Use of Ilizarov Technique in the Correction of Lower Extremity Deformities in Children", see *Orthopedics*, Vol. 20, #7, pages 623–627. The article studied 25 limb treatments with 15 patients. The description, particularly of the complications using the Ilizarov technique of Table 2 at page 625, is specifically incorporated by reference. The article reports that the most common complication was pin tract infection in 11 patients, and that this comprised 52% of the complications occurring in 44% of the limb segments.

Following the regular procedure here described in the newly standardized written description of steps, and using the kit here described, 37 protocol patients having external fixators were treated. They required no hospitalization admissions for serious infection; however, one pin was removed for serious infection. These patients had Ilizarov and EBI external fixators. only five of the 37 patients (13.5%) required short term antibiotics for pin site difficulties. Risk incidents and incidents of infection were therefore significantly decreased from the previously reported Ilizarov study of pin tract infection that occurred in 52% of the complications since in the present study using the kit and procedure here described only in 13.5% of the cases did measurable infection occur. This is a dramatic decrease in infection occurrence. Moreover, few patients indicated any difficulty in understanding and following the instructions, further making patient compliance more likely.

As earlier mentioned, besides the new standardized method herein demonstrated time after time as decreasing infection risk, the invention also contemplates a therapeutic kit for use by physicians in conjunction with their patient treatments. Such a kit as here described may be stocked by hospital pharmacies, emergency rooms, etc. for immediate and convenient use. In general, the kit comprises a sealable, refillable kit container having a series of compartments that contain a plurality of labeled treatment materials as earlier described which are for post-operative cleansing and infection treatment of external pin fixators. Also contained in the kit are written instructions coordinated with the labeled materials describing a uniform treatment regimen as earlier described herein which is to be consistently and regularly employed, preferably twice a day.

From the above examples it can be seen that the invention is successful, its best mode has been described herein, and the patient use examples demonstrate effectiveness.

The examples herein, however, are not intended to be limiting, but only illustrative, and Applicants intend to claim the full range of equivalents they are entitled to under the law with respect to any changes, modifications and alterations that others might make in the kit assembly and the procedure, while still attaining the advantages of the invention herein described.

What is claimed is:

1. A kit for pin care for infection treatment at the interface between pins of an external orthopedic fixation device and a patient's skin, comprising:

a portable, refillable kit container having a series of compartments;

a plurality of labeled treatment materials located in said series of compartments for post-operative cleaning and infection treatment at the interface of external pin fixation devices and patient's skin;

written instructions coordinated with the labeled materials describing a uniform treatment regimen to be consistently and regularly employed, using the plurality of labeled treatment materials placed in said kit; and warning instructions of signs of complications to allow the patient to personally monitor her condition.

2. The kit of claim 1 which includes an instructional video.

3. The kit of claim 1 which includes daily treatment log sheets with the written instructions.

4. The kit of claim 3 which includes sponges and clips to be changed with each cleaning.

5. The kit of claim 4 which includes an anti-microbial cleansing solution.

6. The kit of claim 5 which includes forceps for removing and inserting sponges.

7. A method of decreasing infection risk with external orthopedic fixation devices while increasing patient compliance with a uniform post-operative cleansing and infection treatment regimen, comprising:

providing a portable kit containing a plurality of labeled treatment materials for post-operative cleansing and infection treatment at the interface of external pin fixation devices and a patient's skin;

providing a series of written instructions in the same kit as the labeled treatment materials which describe a uniform post-operative cleansing and infection treatment regimen to be practiced using the labeled treatment materials of said kit; and post-operatively treating the pin/skin interface using the labeled materials from the kit in the manner described in the written instructions.

8. The method of claim 7 wherein the post-operative treating of the pin/skin interface occurs twice daily.

9. The process of claim 8 wherein each pin/skin entry site is first cleansed with sterile water to remove drainage, dried blood or tissue build-up, followed by anti-microbial cleanser treatment of the pin/skin entry site, followed by application of new sponges.

* * * * *